United States Patent [19]

Sakao et al.

[11] Patent Number: 4,487,033
[45] Date of Patent: Dec. 11, 1984

[54] METHOD OF FREEZING FERTILIZED OVA, SPERMATOZOA OR THE LIKE AND APPARATUS THEREFOR

[75] Inventors: Nobuo Sakao; Yasuo Kuraoka, both of Sapporo, Japan

[73] Assignee: Hoxan Corporation, Sapporo, Japan

[21] Appl. No.: 533,932

[22] Filed: Oct. 26, 1983

Related U.S. Application Data

[62] Division of Ser. No. 404,400, Aug. 2, 1982, Pat. No. 4,429,542.

[30] Foreign Application Priority Data

| Aug. 10, 1981 | [JP] | Japan | 56-124996 |
| Aug. 10, 1981 | [JP] | Japan | 56-124997 |
| Sep. 16, 1981 | [JP] | Japan | 56-137410[U] |
| Nov. 18, 1981 | [JP] | Japan | 56-184815 |
| Jan. 14, 1982 | [JP] | Japan | 57-3761[U] |
| Mar. 12, 1982 | [JP] | Japan | 57-34839[U] |

[51] Int. Cl.³ .................................. F25D 17/02
[52] U.S. Cl. .................................. 62/373; 62/430; 62/514 R
[58] Field of Search .................. 62/62, 64, 78, 430, 62/514 R, 65, 96, 373

[56] References Cited

U.S. PATENT DOCUMENTS

| 3,943,993 | 3/1976 | Smith | 62/64 |
| 4,059,967 | 11/1977 | Rowe et al. | 62/78 |
| 4,155,331 | 5/1979 | Lawrence et al. | 62/64 |
| 4,199,022 | 4/1980 | Senkan et al. | 62/78 |
| 4,232,453 | 11/1980 | Edalmann | 62/514 R |
| 4,377,077 | 3/1983 | Granlund | 62/78 |

Primary Examiner—Ronald C. Capossela
Attorney, Agent, or Firm—George B. Oujevolk

[57] ABSTRACT

A method of freezing fertilized ova, spermatozoa or the like which has the steps of containing fertilized ova, spermatozoa or the like in a buffer solution at an irregular position in a tube, and cooling the same so that a buffer solution contained in the area containing no fertilized ova, spermatozoa or the like become lower in temperature than the buffer solution containing the fertilized ova, spermatozoa or the like with a desired refrigerant to freeze the second buffer solution to produce crystalline nuclei, and then cooling the nuclei so that the nuclei grow to the first buffer solution. And, an apparatus for freezing fertilized ova, spermatozoa or the like which can carry out the above method. Thus, the survival rate of the fertilized ova, spermatozoa or the like can be raised, and the fertilized ova, spermatozoa or the like can be readily frozen under an automatic control by simple cooling means.

7 Claims, 16 Drawing Figures

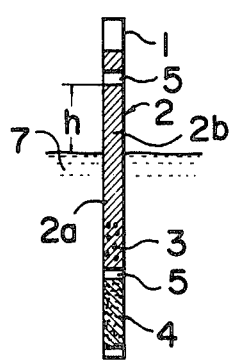
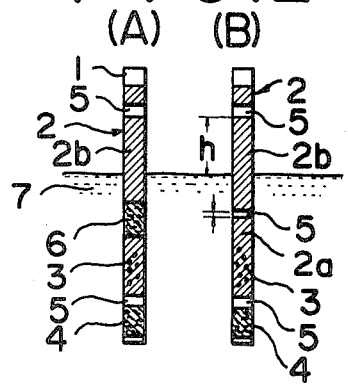
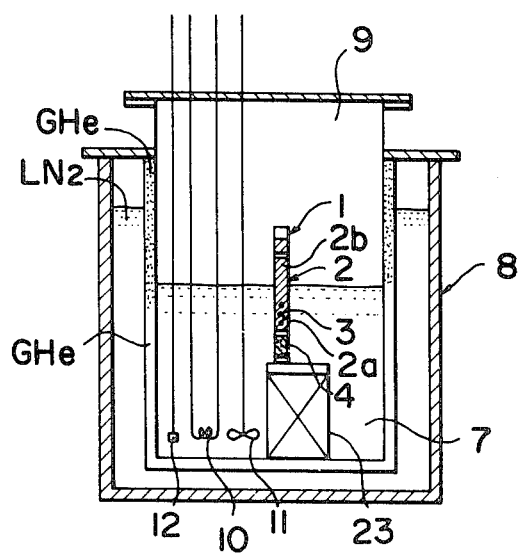

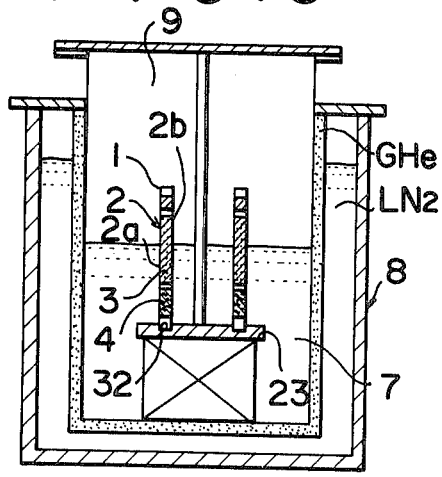
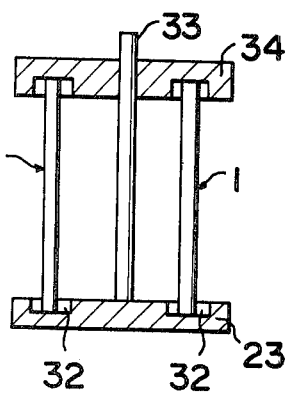
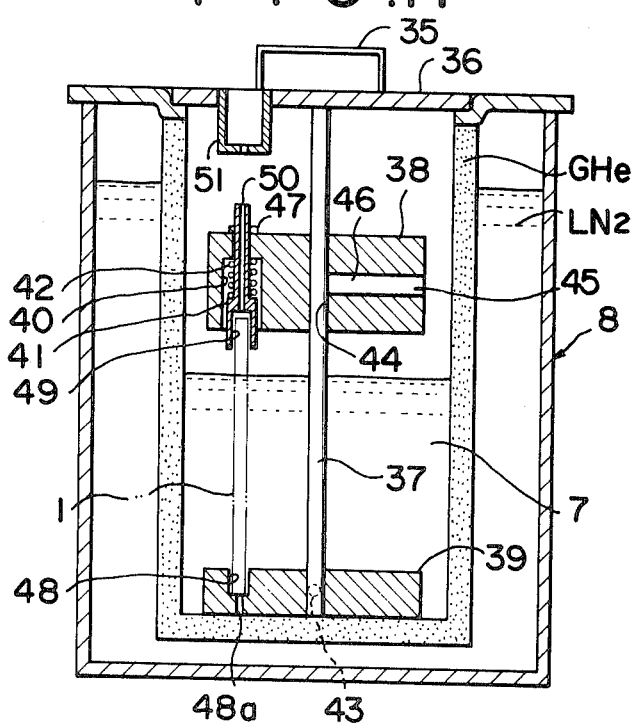

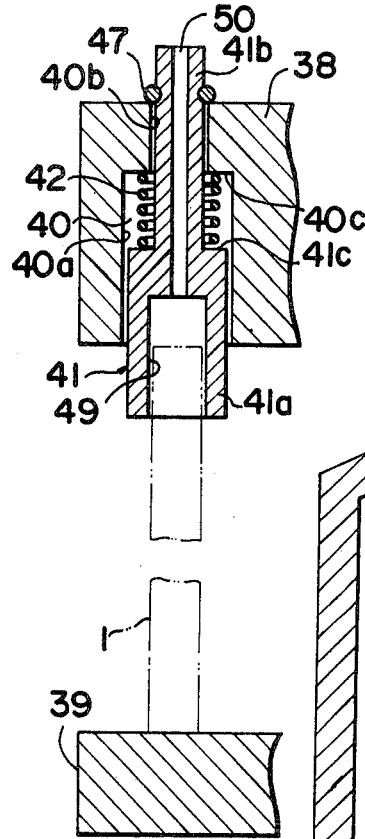
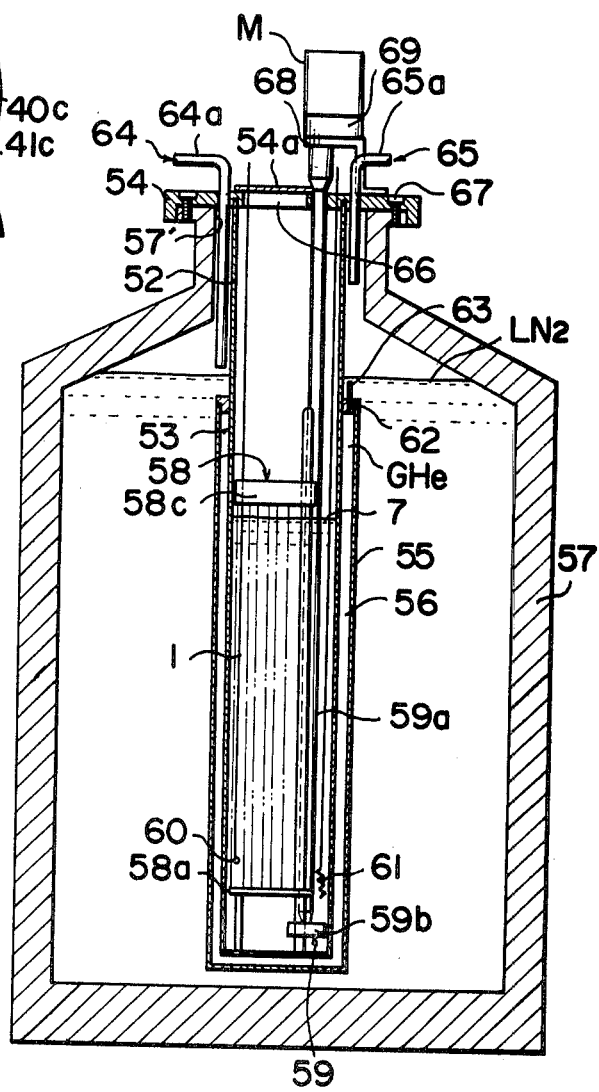

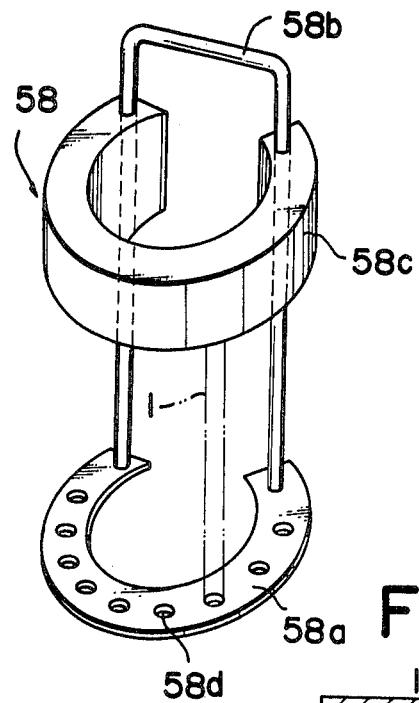
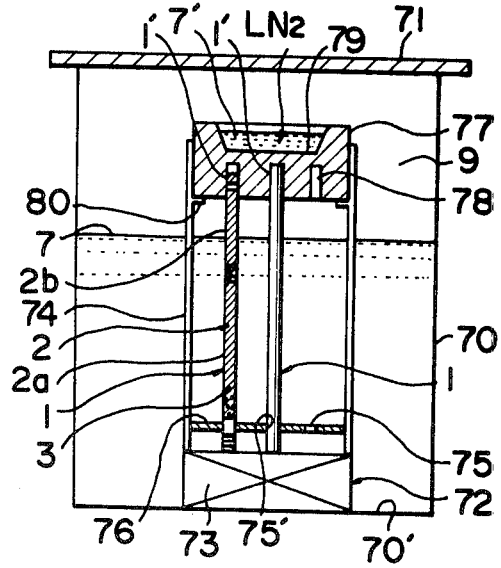

METHOD OF FREEZING FERTILIZED OVA, SPERMATOZOA OR THE LIKE AND APPARATUS THEREFOR

This is a division of application Ser. No. 404,400, filed Aug. 2, 1982, now U.S. Pat. No. 4,429,542, issued Feb. 7, 1984.

BACKGROUND OF THE INVENTION

This invention relates to a novel method of freezing fertilized ova, spermatozoa or the like and an apparatus for freezing the same adapted for carrying out the same method.

An artificial fertilization has been recently carried frequently out to contrive the improvements of breed of domestic animal and of growth of the domestic animal. In this case, fertilized ova and spermatozoa have been preserved by freezing the same.

It was heretofore known to fill the fertilized ova and spermatozoa in a buffer solution contained in a tube and to freeze the buffer solution as a method of freezing the fertilized ova and spermatozoa.

A temperature change with respect to time of a pure substance when the substance is cooled under a constant pressure is generally known as a cooling curve. According to this principle, the substance does not always start immediately freezing when the substance reaches its freezing point, but the substance will start generally freezing after the substance is overcooled to the temperature lower than its freezing point. Simultaneously, the substance raises its temperature to its true freezing point, and the substance will then lower its temperature again after the entire substance is completely frozen.

The buffer solution is overcooled at the freezing time in the freezing step according to the above-mentioned conventional freezing method which merely cools the substance. Then, the temperature of the substance or buffer solution is thereafter immediately raised. Therefore, the fertilized ova and spermatozoa are dead due to the thermal shock of this abrupt temperature change according to the conventional freezing method.

It has been proposed to avoid such a thermal shock by a method of freezing fertilized ova and spermatozoa to remove the buffer solution cooled to the freezing point and to holding a tube containing the buffer solution with a pincette preserved in liquefied nitrogen, thereby carrying out the freezing from the holding position. This also lacks actual utilization due to the fact that the removal of the tube adversely affects the temperature of the buffer solution so that there is a failure in the freezing of the solution and an automatic control is difficult due to the complicated operations.

SUMMARY OF THE INVENTION

Accordingly, a primary object of this invention is to provide a method of freezing fertilized ova, spermatozoa or the like which can eliminate the aforementioned drawbacks and disadvantages of the conventional freezing method and can raise the survival rate of the fertilized ova, spermatozoa or the like by enabling the freezing of the same without cooling the same to overcooled state.

Another object of this invention is to provide a method of freezing fertilized ova, spermatozoa or the like which can readily carry out an automatic control with simple cooling means.

Yet another object of this invention is to provide a method of freezing fertilized ova, spermatozoa or the like which can improve its workability by suitably determining the refrigerant temperature for the temperature control of the solution.

Still another object of this invention is to provide an apparatus for freezing fertilized ove, spermatozoa or the like which can adequately carry out the above-mentioned method.

Still another object of this invention is to provide an apparatus for freezing fertilized ova, spermatozoa or the like which can maintain a tube containing buffer solution in a dipped state in a refrigerant so as to carry out the foregoing method.

These and other related objects and features of the invention will be apparent from a reading of the following description of the disclosure taken together with the accompanying drawings and the novelty thereof pointed out in the appended claims.

BRIEF DESCRIPTION OF THE DRAWINGS

FIG. 1 is a front, longitudinally sectional explanatory view of a tube containing fertilized ova, spermatozoa or the like used in a method of freezing the fertilized ova, spermatozoa or the like according to the present invention;

FIGS. 2A and 2B are front, longitudinally sectional explanatory views of modified examples of the tube containing fertilized ova, spermatozoa or the like according to the present invention;

FIGS. 3 and 5 are front, longitudinally sectional views of apparatuses for freezing fertilized ova, spermatozoa or the like to carry out the method of freezing the same according to the present invention;

FIG. 9 is a front, longitudinally sectional view of a temporarily installed freezing apparatus to strengthen the features of the apparatus shown in FIG. 8;

FIG. 10 is a front, longitudinally sectional view of a tube holding mechanism used in the apparatus shown in FIG. 8 to strengthen the features thereof;

FIG. 11 is a front, longitudinally sectional view showing a further preferred embodiment of an apparatus for freezing fertilized ova, spermatozoa or the like used to carry out the method of the present invention;

FIG. 12 is a front, enlarged longitudinally sectional view of modified embodiment of the apparatus according to the present invention;

FIG. 13 is a front, longitudinally sectional view showing still another preferred embodiment of an apparatus for freezing fertilized ova, spermatozoa or the like used in the method of the present invention;

FIG. 14 is a perspective view of the tube holding mechanism of the apparatus according to the present invention; and FIG. 15 is a front, longitudinally sectional view showing still another preferred embodiment of an apparatus for freezing fertilized ova, spermatozoa or the like used in the method of the present invention.

DESCRIPTION OF THE PREFERRED EMBODIMENTS

Figure 4:
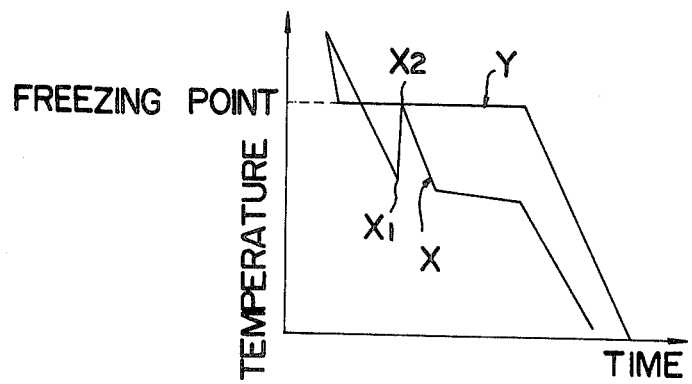
FIG. 4 is a graph showing the cooling curve of a buffer solution used in the method according to the present invention.

The present invention will now be described in more detail with reference to the accompanying drawings.

Referring first to FIGS. 1 through 5, which show one preferred embodiment of a method of freezing fertilized ova, spermatozoa or the like according to the present invention and one preferred embodiment of an apparatus for carrying out the same method, wherein like reference numerals designate the same or equivalent parts in the following views, a buffer solution 2 is prepared by dissolving, for example, dimethyl sulfoxide (DMSO), dextrose, glycerin and/or sodium citrate in a distilled water, the buffer solution 2 thus prepared is filled in a tube 1, e.g., a straw tube as shown in FIG. 1, and articles 3 to be frozen, e.g., fertilized ova, spermatozoa or the like are thrown to the buffer solution 2.

In this case, a cotton plug 4 or the like is charged in the lower end of the tube 1, and the articles 3 to be frozen are, on the other hand, contained at irregular position as substantially lower half portion of the buffer solution 2 in the lower end of the tube 1.

When it is desired to contain the fertilized ova, spermatozoa or the like in one of divided buffer solution segments of the buffer solution by dividing the buffer solution into a plurality of buffer solution segments, segmenting gaps 5 may be formed with air bubbles at suitable position or positions of the buffer solution 2 as shown in FIGS. 1 and 2B or a cotton plug may be engaged as a segmenting gap in the tube as shown in FIG. 2A. In this case, the gaps 5 are formed substantially within 2 mm.

When the tube 1 is then cooled according to the present invention, the entirety of the tube 1 is not cooled, but the difference of phases is provided at the cooling temperature between a buffer solution segment 2a containing the fertilized ova, spermatozoa or the like as the articles 3 to be frozen in the lower portion of the tube 1 and a buffer solution segment 2b containing no article 3 in the upper portion of the tube 1, the buffer solution segment 2b is first frozen to form crystalline nuclei, and the crystalline nuclei thus produced are then grown to the buffer solution segment 2a, thereby freezing the articles 3, e.g., the fertilized ova, spermatozoa or the like.

Figure 5:
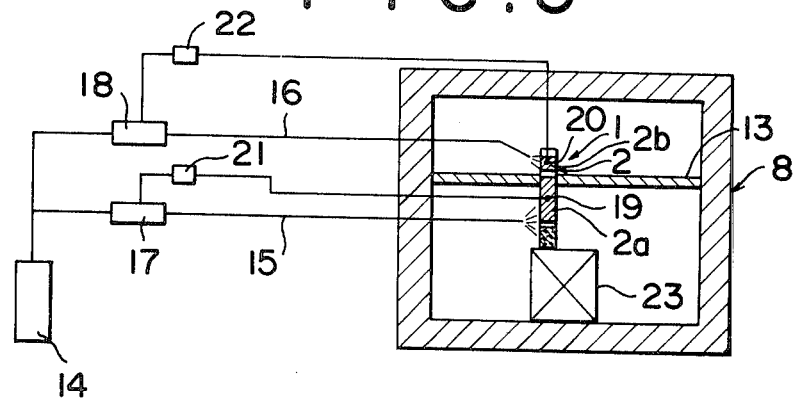

FIGS. 3 and 5 show one and another preferred embodiments of an apparatus for freezing fertilized ova, spermatozoa or the like to carry out a method of freezing the same according to the present invention. FIG. 3 shows one preferred embodiment of the apparatus of the invention which has a double wall low constant temperature tank 8 containing refrigerant 7 therein, in which a tube 1 is so arranged that the buffer solution segment 2a is dipped in the refrigerant 7 and the buffer solution segment 2b is submerged in the refrigerant 7 in such a manner that the buffer solution segment 2b is projected from the surface of the solution of the refrigerant 7 into a vapor phase section 9, and the height h from the liquid surface to the segmenting gap 5 is preferably, as shown in FIGS. 1 and 2, larger than approx. 30 mm.

In the apparatus of this embodiment, LN, He gas or the like is contained in the space between the double walls of the low constant temperature tank 8, and the refrigerant 7 may include, for example, isopentane, etc. The apparatus of this embodiment further has a heater 10, an agitator 11 and a temperature sensing element 12 arranged in the refrigerant 7. The temperature of the refrigerant 7 is controlled by a controller (not shown) so that the buffer solution 2 is maintained, at its freezing point (e.g., −4.2° C.).

As just described, the temperature of the buffer solution 2 is maintained constantly at the freezing point. In this case, vaporized refrigerant is sufficiently occupied in the vapor phase section 9 of the low constant temperature tank 8, with the result that the buffer solution 2 is decreased at its temperature than the refrigerant 7, i.e., to the lowered temperature by approx. −30° C. with respect to the freezing point of the buffer solution 2.

Accordingly, the buffer solution segment 2b located above the liquid surface of the refrigerant 7 becomes overcooled state due to the process designated by a cooling curve X in FIG. 4, and is frozen upon an abrupt temperature rise from the overcooled point X1.

On the other hand, the buffer solution segment 2a in the refrigerant 7 is not affected by the influence of the above-mentioned temperature rise of the buffer solution segment 2b, but is maintained at the constant temperature of the freezing point as designated by a cooling curve Y in FIG. 4.

In this manner, crystalline nuclei are produced by the freezing of the buffer solution segment 2b as described above, and are grown to the buffer solution segment 2a.

It is noted in this case to aid the growth of the crystalline nuclei that the temperature of the refrigerant 7 is preferably lowered gradually. Thus, the crystalline nuclei are abruptly grown into the buffer solution segment 2a, and the buffer solution segment 2a in the refrigerant 7 is frozen without becoming overcooled state.

The temperature X2 in FIG. 4 is the starting point of freezing of the buffer solution segment 2b and hence the starting point of freezing of the buffer solution 2a. After the buffer solution segment 2a has completely been frozen at the freezing point, its temperature is lowered to approx. −100° C. by the refrigerant 7 as illustrated by the cooling curve Y, and the tube 1 is preserved in the liquefied nitrogen.

In the apparatus of the embodiment shown in FIG. 5, a tube 1 contained in a low constant temperature tank 8 is divided or partitioned to upper and lower sections by a partition plate 13 in the tank 8. The buffer solution segment 2a contained in the tube 1 is cooled to desired temperature (freezing point) as described above by the refrigerant from a liquefied gas source 14, and the buffer solution segment 2b contained in the upper portion is frozen with the refrigerant from the liquefied gas source 14 individually. Thus, crystalline nuclei are produced therein, and the buffer solution segment 2a is thus cooled at the constant temperature as it is, or is gradually lowered at its temperature to grow the crystal so as to freeze articles 3 to be frozen, e.g., fertilized ova, spermatozoa or the like by freezing the buffer solution segment 2a, and is lowered to the desired temperature as described above.

In the apparatus of the embodiment shown in FIG. 5, there are arranged refrigerant supply lines 15, 16 from the liquefied gas source 14 to the low constant temperature tank 8, heat exchangers 17, 18 arranged respectively at the refrigerant supply lines 15, 16, temperature detectors 19, 20 provided in the buffer solution segments 2a and 2b in the tube 2 for sensing the temperatures of the respective buffer solution segments 2a and 2b, and temperature controllers 21 and 22 connected respectively to the temperature detectors 19 and 20 at one ends and also connected respectively to the heat exchangers 17 and 18 for controlling the heat exchangers 17 and 18 to control the temperatures of the buffer solution segments 2a and 2b to desired temperatures, respectively. In this manner, the temperature of the refrigerant corresponding respectively to the buffer solution segments 2a and 2b is individually controlled.

As herein before described, according to the preferred embodiment of the method of freezing fertilized ova, spermatozoa or the like in accordance with the present invention, the buffer solution segment 2a containing the fertilized ova, spermatozoa or the like are cooled, but are not frozen, and the buffer solution segment 2b is first frozen by the refrigerant. Then, the crystalline nuclei thus obtained are grown toward the buffer solution segment 2a, thereby freezing the buffer solution segment 2a indirectly. Therefore, the buffer solution segment 2a containing the fertilized ova, spermatozoa or the like is not overcooled in the freezing course of the fertilized ova, spermatozoa or the like, but is frozen. Thus, the death of the fertilized ova, spermatozoa or the like due to the abrupt temperature rise can be avoided, thereby performing the freezing of the fertilized ova, spermatozoa or the like with high survival rate, performing the method with various types of suitable apparatuses, and introducing an automatic control to the apparatuses adapted for mass production.

In case of freezing fertilized ova, spermatozoa or the like as described above, various types of buffer solutions 2 contained in the tube 1 may be actually employed. At that time, the temperature of the coolant for controlling the temperature of the buffer solution should be determined every time different buffer solution is used to hole the buffer solution segment 2b contained as above at its freezing point. Accordingly, it is necessary to measure the freezing point of the buffer solution and to set the control temperature based on the measured value.

This causes complicated freezing work and cannot accordingly expect the efficient treatment. Therefore, the embodiment of the method of freezing fertilized ova, spermatozoa or the like described above is further improved as below to remarkably improve the workability of the method in view of the complicated freezing operation.

Figure 6:
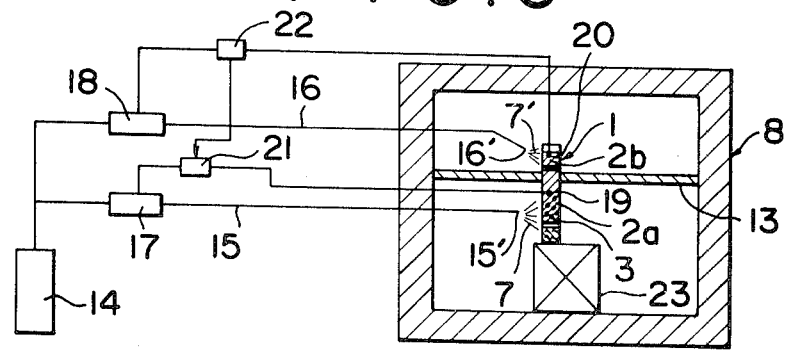
FIG. 6 is an overall explanatory view of an apparatus for freezing fertilized ova, spermatozoa or the like used in a method of freezing the same according to another preferred embodiment of the present invention.
Figure 7:
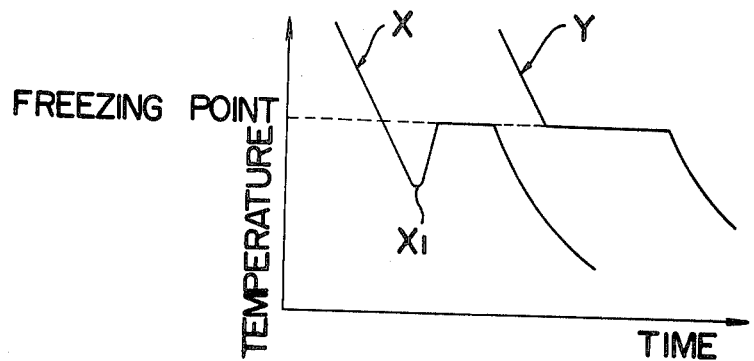
FIG. 7 is a graph showing the cooling curves of a buffer solution contained in the area containing no fertilized ova, spermatozoa or the like in a tube containing the same and another buffer solution containing the same in the tube with respect to the time.

Referring now to FIGS. 6 and 7, which show another preferred embodiment of a method of freezing fertilized ova, spermatozoa or the like according to the present invention, the fundamental constitution of the apparatus for carrying out the method of this embodiment is, as shown in FIG. 6, similar to that shown in FIG. 5. The buffer solution segment 2a containing articles 3 to be frozen, e.g., fertilized ova, spermatozoa or the like is located in the lower portion of a partition plate 13 installed in a low constant temperature tank 8 and is cooled by refrigerant 7 contained therein, and the buffer solution segment 2b is located in the upper portion of the partition plate 13 and is cooled by the refrigerant 7' contained therein. According to this embodiment of the method of the present invention, the refrigerants 7, 7' are supplied from a liquefied gas source 14 by the constitution described below. The refrigerant 7 is first supplied through a lower refrigerant supply line 15 interposed with a heat exchanger 17 in the midway of the lower supply line 15 and is injected from a nozzle 15' provided at the end of the lower supply line 15 toward the buffer solution segment 2a. A temperature detector 19 is further provided in the buffer solution segment 2a in the tube 1 for sensing the temperature of the buffer solution segment 2a, and a temperature controller 21 is connected at its one end to the temperature detector 19 and is also connected at its other end to the heat exchanger 17 for controlling a current to a heat source (not shown), e.g., an electric heater or the like of the heat exchanger 17.

On the other hand, the refrigerant 7' is similarly supplied through an upper refrigerant supply line 16 interposed with a heat exchanger 18 in the midway of the upper supply line 16 and is injected from a nozzle 16' provided at the end of the upper supply line 16 toward the buffer solution segment 2b. A temperature detector 20 is further provided in the buffer solution segment 2b in the tube 1 for sensing the temperature of the buffer solution segment 2b, and a temperature controller 22 is connected at its one end to the temperature detector 20 and is also connected at its other end to the heat exchanger 18 for controlling a current to a heat source (not shown). Further, both the temperature controllers 21 and 22 are connected to one another, and thus the measured value of the temperature as the maximum value is applied as the set temperature value to be controlled by the temperature controller 21 when the incoming detection signal from the temperature detector to the temperature controller 22 becomes the maximum value.

In the construction of the apparatus of this embodiment for carrying out the method of this embodiment, articles 3 to be frozen, e.g., fertilized ova, spermatozoa or the like are frozen with this apparatus by the steps of containing the tube 1 in the low constant temperature tank 8 as described above, and then supplying the refrigerants 7, 7' of liquefied gas from the liquefied gas source 14 through the refrigerant supply lines 15, 16 to the low constant temperature tank 18 to thereby individually lower the temperatures of the buffer solution segments 2a and 2b. In this case, the temperature of the refrigerant 7' is sufficiently lowered, the temperature of the buffer solution segment 2b is thus lowered as shown by the cooling curve X in FIG. 7 to the overcooled state under the freezing point thereof, the buffer solution segment 2b is then frozen upon abrupt temperature rise from the overcooled point X1 in FIG. 7, and crystalline nuclei are thus produced.

When the freezing is thus started as described above, it is maintained at the maximum temperature until the buffer solution segment 2b is completely frozen, the temperature of the buffer solution segment 2b exhibits the freezing point of the buffer solution 2, the temperature detector 20 which detects this freezing point produces and applies the detection signal from the temperature controller 20 to the temperature controller 21, the controller 21 further controls the heat exchanger 17 with the temperature, e.g., the temperature lower actually by approx. 0.5° C. from the freezing point of the measured temperature, and the temperature of the buffer solution segment 2a is controlled by cooling with the refrigerant 7 to the vicinity of the freezing point as designated by the cooling curve Y in FIG. 7.

As hereinbefore described, the crystalline nuclei produced in the buffer solution segment 2b are grown to the buffer solution segment 2a maintained at the vicinity of the freezing point, and the buffer solution segment 2a is accordingly frozen without becoming overcooled state to freeze the articles 3 to be frozen, e.g., fertilized ova, spermatozoa or the like.

As the foregoing description, according to the foregoing embodiment of the present invention, the freezing point of the buffer solution is measured by utilizing the freezing point of the buffer solution segment containing no articles to be frozen, e.g., fertilized ova, spermatozoa or the like, and the temperature of the buffer solution segment containing the articles to be frozen, e.g., fertilized ova, spermatozoa or the like is automatically controlled in this manner. Therefore, it becomes unnecessary to measure the freezing point of the buffer solutions of various types to be used separately, and can accordingly perform efficient freezing step. Further, it can automate the setting of the optimum conditions of producing crystalline nuclei and can accordingly prove always the performance of the desired freezing of the articles to be frozen, e.g., fertilized ova, spermatozoa or the like.

As described, one embodiment of the apparatus for freezing fertilized ova, spermatozoa or the like for carrying out one embodiment of the method of freezing the same has already been disclosed with respect to FIG. 3.

However, the apparatus of this embodiment merely has a base 23 which merely places the refrigerant 7, and the tube 1 is merely held therein in an erected state. When the volume of the refrigerant 7 is varied in this case, the level of the liquid of the refrigerant 7 will naturally vary, with the result that the height of the liquid phase with respect to the vapor phase to the tube 1 will change. Accordingly, the elevational movement of the surface of the refrigerant liquid causes improper freezing of the buffer solution or excessively low liquid level causes adverse influence to the articles to be frozen, e.g., fertilized ova, spermatozoa or the like upon freezing disadvantageously. In order to eliminate such states, it is necessary as a problem to always monitor the liquid level of the refrigerant 7 and to suitably maintain the liquid level by supplying the refrigerant 7.

Figure 8:
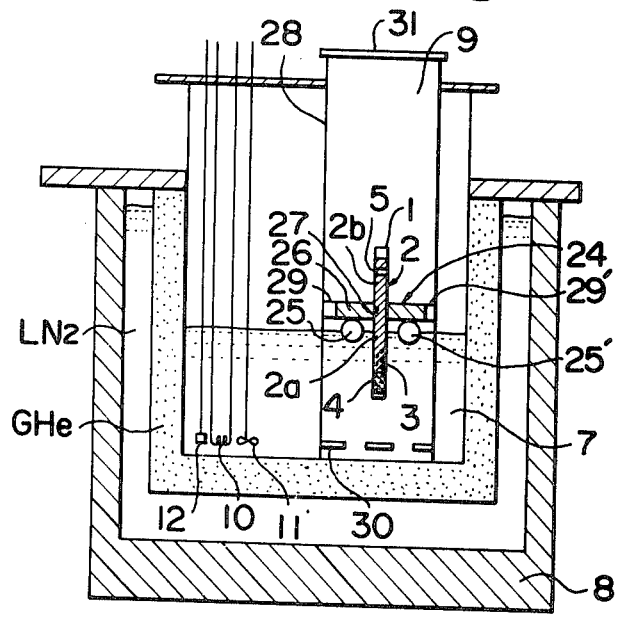
FIG. 8 is a front, longitudinally sectional view showing yet another preferred embodiment of an apparatus for freezing fertilized ova, spermatozoa or the like used to carry out the method of the first preferred embodiment of the present invention.

This problem can be overcome by yet another preferred embodiment of an apparatus for freezing fertilized ova, spermatozoa or the like for performing the above embodiment of the method of the present invention with reference to FIG. 8, wherein the like reference numerals in FIG. 8 to those in FIG. 3 designate the same or equivalent parts or components in FIG. 3, and the difference between this embodiment and the previous embodiment shown in FIG. 3 is the construction that a floating base 24 is floated on the liquid surface of the refrigerant 7, the tube 1 is passed through the floating base 24 substantially perpendicularly thereto as shown, the floating base 24 consists of floats 25 and 25' and a through hole plate 26 placed on the floats 25 and 25' with the tube 1 supported through the penetrating hole 27 of the through hole plate 26. The tube 1 is projected from the through hole plate 26 at a predetermined length, for example, by approx. 30 mm, and the buffer solution segment 2a containing the articles 3 to be frozen, e.g., fertilized ova, spermatozoa or the like is dipped in the refrigerant 7.

The apparatus of this embodiment further has a guide column 28 inserted and erected in the refrigerant 7 and containing the floating base 24 therein, guide elements 29, 29' slidably provided on the inner wall of the guide column 28, at which slits 30 are formed at the lower portion for flowing the refrigerant 7 into or out of the column 28, and a cover plate 31 covered on the top of the guide column 28.

Therefore, even if the volume of the refrigerant 7 is varied, causing the variation in the liquid level of the refrigerant 7, the floating base 24 will elevationally move in accordance with the change in the liquid level of the refrigerant 7. In this manner, the vapor phase length and the liquid phase length of the tube 1 can be maintained always constantly. The guide column 28 thus provided as shown in FIG. 8 is thus provided, and the floating base 24 is guided in the guide column 28 elevationally therein. Thus, even if the liquid level of the refrigerant 7 is varied or fluctuated, the floating base 24 will now largely fluctuate, and accordingly the vapor phase and liquid phase of the tube 1 can be more desirably stabilized satisfactorily.

As just described, according to this embodiment of the apparatus thus constructed for executing the method of freezing fertilized ova, spermatozoa or the like in accordance with the present invention, the floating base 24 is floated on the liquid surface of the refrigerant 7, the tube 1 is inserted and supported in the floating base 24, the buffer solution segment 2b containing fertilized ova, spermatozoa or the like of the tube 1 extends upwardly from the floating base 24 in a predetermined length in the vapor phase portion, and the buffer solution segment 2a containing no fertilized ova, spermatozoa or the like extends from the floating base 24 downwardly in a predetermined length to the refrigerant 7 to be dipped therein. Therefore, even if the volume of the refrigerant 7 is varied, the vapor phase and the liquid phase of the tube 1 can be always maintained and uniformalized in a desired predetermined length, with the result that the preferably freezing of the articles to be frozen, e.g., fertilized ova, spermatozoa or the like can be proved, thereby eliminating the necessity of performing the complicated works such as monitor of the liquid level of the refrigerant 7 and supply of refrigerant or the like to the tube containing buffer solution including fertilized ova, spermatozoa or the like as well as the expensive addtional arrangements.

In the apparatus of the embodiment shown in FIG. 3, the tube 1 is merely placed on the base 23 as shown, but the tube 1 cannot actually be erected only with this arrangement. Therefore, the simplest means for holding the tube 1 will be described with reference to FIG. 9 so as to firmly erect the tube on the base 23.

In FIG. 9, the base 23 is formed of a metallic plate, and a recess or recesses 32 are formed on the upper surface of the plate 23 for engaging the bottom of the tube 1. When the base 23 is pulled up from the refrigerant 7, moisture contained in the atmospheric air is condensed on the metallic plate 23 maintained at low temperature and is frozen, with the result that the tube 1 is iced with the recess 32 formed on the metallic plate 23, and when the tube 1 is removed from the base 23, the tube 1 cannot be removed from the recess 32.

Therefore, the holes 32 formed on the upper surface of the metallic plate or base 23 are so formed, as shown in FIG. 10, in a diameter larger than that of the bottom of the tube 1 as not to ice and secure the tube 1 to the recess. In this construction even if the tube 1 is not fallen down, the tube 1 will float by the buoyancy of the refrigerant 7. Accordingly, a weight plate 34 is elevationally movably arranged at a guide rod 33 stood from the base or metallic plate 23 to thereby urge down the tube or tubes 1 onto the base or metallic plate 23, thereby preventing the tubes 1 from floating in the refrigerant 7.

In the arrangement described above of the apparatus of this embodiment, the recesses 32 are formed larger than the size of the tube 1 on the base or metallic plate 23. Therefore, when a number of tubes 1 are provided, the tubes 1 might feasibly fall down. Accordingly, the tubes 1 must be installed between the base or metallic plate 23 and the weight plate 34 one by one by charging the tubes therebetween, causing much labor and time therefor.

This problem can be overcome by a further embodiment of the apparatus for freezing articles to be frozen, e.g., fertilized ova, spermatozoa or the like for executing the method of the present invention as shown in FIGS. 11 and 12, in which freezing of tubes to the base or metallic plate due to freezing of the moisture contained in the atmospheric air can be prevented, floating or fluctuating of the tubes from the base or metallic plate is overcome but the tubes can be firmly secured to the base or metallic plate, and the tubes can be simply and rapidly charged without much labor and time consumption.

In FIGS. 11 and 12, the apparatus of this embodiment has a low constant temperature tank 8 containing refrigerant such as $LN_2$, or GHe similarly to the structure of the previous embodiments of the apparatus, a cover plate 36 to be an upper cover of the tank 8 with a handle 35 attached thereonto, a guide rod 37 perpendicularly secured to the center on the back surface of the cover plate 36, upper and lower mounting members 38 and 39 mounted at a predetermined interval therebetween at the upper and lower portions of the guide rod 37, and a tube holding slide pin 41 formed of synthetic resin, e.g., Teflon (trade name) and inserted through the mounting through hole 40 of the upper mounting member 38 with a coiled spring 42 mounted around the slide pin 41 to urge downwardly the slide pin 41 to be elevationally movably for elastically holding the tube 1 between the lower mounting member 39 and the slide pin 41.

The upper and lower mounting members 38 and 39 are formed of synthetic resin, e.g., Teflon (trade name), thereby preventing icing with moisture contained in the atmospheric air of a straw tube 1, and are also arranged to hold the tube 1 of different length in such a manner that these members 38 and 39 are relatively movably therebetween to approach to each other or to isolate from each other between the upper and the lower mounting members 38 and 39 onto the guide rod 37.

In other words, in the apparatus of this embodiment, the lower mounting member 39 is clamped with clamping screw 43 to the guide rod 37, and the upper mounting member 39 is elevationally movably adjustably mounted to the guide rod 37 by the arrangement that a threaded hole 45 reaching the inserting hole 44 of the guide rod 37 formed on the guide rod 37 is laterally perforated at the upper mounting member 38, and a clamping screw 46 is engaged into the threaded hole 45, thereby securing the upper mounting member 38 at a desired predetermined position in the elevational direction to the guide rod 37.

The mounting hole 40 of the upper mounting member 39 and the slide pin 41 are so correspondingly formed that the larger-diameter portions 40a, 41a are formed at the lower portions thereof and the smaller-diameter portions 40b and 41b are correspondingly formed at the upper portions thereof, the spring 42 is interposed between the downward stepped portion 40c of the mounting hole 40 of the upper mounting member 38 and the shoulder portion 41c of the slide pin 41, the slide pin 41 is downwardly elastically urged to the upper mounting member 38, and an O-ring 47 for preventing the slide pin 41 from falling into the hole of the upper mounting member 39 is engaged at the projecting end of the small-diameter portion 41b of the slide pin 41 to prevent the slide pin 41 from falling from the upper mounting member 38.

A plurality of slide pins 41 may be preferably supported to the upper mounting member 38 similarly to the above arrangement, and in this case, a plurality of mounting holes 40 may be perforated at equal interval along the imaginary circular peripheral line around the inserting hole 44 as a center, and the slide pin 41 may be respectively supported at the mounting holes 40.

The bearing recesses of the tubes 1 at the lower mounting member 39 may be formed as mere recesses 48 as shown in FIG. 11, and may also be formed as mere flat smooth surface as shown in FIG. 12.

In case of the bearing recesses 48 formed on the upper surface of the lower mounting member 39, the recesses 48 may be preferably formed in the diameter larger than that of the tubes 1 to be readily inserted with the tube 1, and a drain hole 48a may preferably be formed from the bottom of each recess 48 to the bottom to communicate the refrigerant 7 so as to avoid the retention of the refrigerant 7 therein.

On the bottom surface of the slide pin 41 are perforated an inserting recess 49 for supporting the tube 1 in downward opening at the center, and a sensor hole 50 opened on the top surface in upward opening communicating through the longitudinal slide rod 41.

In this case, the diameter of the inserting recess 49 for supporting the tube 1 may be preferably formed sufficiently larger than that of the tube 1.

When the slide pin 41 is thus formed, the upper end of the tube 1 may be preferably inserted into the inserting recess 49, and the tube 1 may be accurately and effectively held at a predetermined position.

A thermometer mounting column 51 is preferably provided at the cover plate 36 directly above the sensor hole 50 of the slide pin 41, a thermometer may be mounted in the column 51, and is mounted from the hole 50 to the tube 1 for detecting the temperature in the tube 1.

As just described, the apparatus of this embodiment for carrying out the method of the present invention according to the present invention is constructed in the arangement that the upper and lower mounting members 38 and 39 made of synthetic resin are mounted at the guide rod 37 perpendicularly installed on the back surface of the cover plate 36, the tube holding slide pin 41 formed of synthetic resin is elastically elevationally movably mounted via the spring 42 at the upper mounting member 38 to urge the guide pin 41 downwardly, and the tube 1 is elastically held between the slide pin 41 and the lower mounting member 39. Therefore, the slide pin 41 can be moved upwardly against the tension of the spring, the tube 1 is placed on the lower mounting member 39, and the upward tension of slide pin 41 is released. Thus, the slide pin 41 is downwardly moved by the tension of the spring to elastically hold the tube 1 between the slide pin 41 and the lower mounting member 39. Accordingly, even when a number of tubes are elastically held between the guide pin and the lower mounting member, the above simple operation may be repeated to rapidly mount the tubes, and yet the floating and the fluctuation of the tubes can be prevented by the elastic mounting of the tubes between the guide pin and the lower mounting member.

Further, synthetic resin is used at suitable members and parts, it can prevent the icing of the members and parts to be mounted. The upper and lower mounting members 38 and 39 are further integrally formed of the cover plate 36 via the guide rod 37, and the tubes 1 can be readily mounted at and removed from the low constant temperature tank 8, and the cover plate may be opened or closed simultaneously upon operation for convenience of practical use.

Still another preferred embodiment of an apparatus for freezing articles to be frozen, e.g., fertilized ova, spermatozoa or the like for performing the method of the present invention will be described with reference to FIGS. 13 and 14.

The apparatuses of the previous various embodiments described above are constructed in the arrangements that the low constant temperature tank fabricated particularly and the controller for the temperature therefor are integrally connected. Therefore, the entire configuration of the apparatus becomes considerably large in size, and is difficult to be moved. Accordingly, fertilized ova, spermatozoa or the like collected at the field should be transported to the special position installed with the apparatus for freezing the same, and should be then set in the apparatus for freezing the same, with the result that the fertilized ova, spermatozoa tend highly to dead in the course of transforming the same, thereby decreasing the yield of the work as drawbacks and disadvantages.

In the apparatus of this embodiment constructed according to the present invention, the apparatus is readily portable so as to overcome the above-mentioned problem, and the portable freezing apparatus is readily capable of being connected to a low temperature liquefied gas container bought even at the field. Thus, the collected fertilized ova, spermatozoa or the like may be immediately frozen in this manner, thereby minimizing the death of the fertilized ova, spermatozoa or the like.

In FIG. 13, the apparatus of this embodiment has an inner tank 53 formed of a column 52 with a bottom, a cover plate 54 placed fixedly on the top of the inner tank 53, an outer tank 56 formed of a column 55 with a bottom having a diameter larger than that of the column 52 and concentrically arranged at the outside of the inner tank 53 to integrate the tanks 53 and 56, which is detachably mounted in a low temperature liquefied gas container 57, which is closed by the cover plate 54 at the opening 57' detachably.

In the inner tank 53 are internally mounted a tube erecting base 58, an agitator 59, a thermometer 60 and a heater 61 as required members, and refrigerant 7 such as Freon or the like contained therein.

On the other hand, in the outer tank 57 are sealed heat exchanging medium, e.g., GHe, etc. The sealing means therefor has a supporting plug 62 for securing the column 55 and the column 52 of the inner tank 53 at the opening of the column 55, and a filling tube 63 mounted in advance at the plug 62. After the medium, e.g., GHe is filled from the tube 63 in the outer tank 57, it is sealed or a valve (not shown) is mounted at the tube 63, and the valve is closed after filling the medium, and the valve is then sealed.

Further, a low temperature liquefied gas supply port 64 and a vaporized gas exit 64 are opened at the cover plate 54 for supplying the liquefied nitrogen LN or the like so as to communicate with the liquefied gas container 57 through pipes 64a, 65a secured through the cover plate 54. When the apparatus of this embodiment is mounted in the container 57 as shown, or during the use of the apparatus, LN or the like is consumed, and the LN should be supplied from the supply port 64 to the container 57. The vaporized gas from the LN may be externally exhausted from the exit 65.

At the cover plate 54 is provided an opening 66 for mounting or dismounting the tube erecting base 58, and at the opening 66 is mounted an openable cover 54a for firmly closing the opening 66.

In the apparatus of this embodiment shown, the cover 54 is detachably secured to the opening edge of the liquefied gas container 57 with a bolt 67.

The tube erecting base 58 is, as obviously shown in FIG. 14, constructed in the arrangement that a guide and handle 58b is stood on a horseshoe-shaped base 58a, a tube holder 58c is elevationally slidably engaged with the erecting portion of the handle 58b, the tube 1 is erected in the recess 58d formed on the upper surface of the base 58a, the top end of the tube 1 is pressed by the holder 58c, thereby enabling to erect a plurality of tubes 1, and the base 58a and the holder 58c are formed in horseshoe shape, thereby eliminating the disturbance of the agitator 59 or the like when filling the tubes into the narrow inner tank 53.

The agitator 59 is constructed to insert its rotational shaft (not shown) into a bearing tube 59a vertically mounted on a supporting base secured to the cover plate 54 and to mount agitating blades 59b to the projecting end of the rotational shaft to be driven rotatably via a reduction gear 69 by a motor M placed on the cover plate 54.

In order to freeze fertilized ova, spermatozoa or the like, cooling heat of $LN_2$ or the like is transferred through GHe or the like to the refrigerant 7, and the temperature of the refrigerant 7 is set to the predetermined conditions known per se by the agitator 59, the thermometer 60, the heater 61 and the like.

As just described, the apparatus of this embodiment according to the present invention is constructed in the arrangement that the cover plate 54 is provided at the upper edge of the inner tank 53 formed to contain the refrigerant 7, e.g., Freon or the like, the outer tank 56 sealing heat exchanging medium, e.g., helium or the like in the outer peripheral space out of the inner tank 53, the tube erecting base 58 is telescopically mounted in the refrigerant 7 in the inner tank 53, the agitator 59, heater 61, and thermometer 60 and the like are internally mounted as predetermined required members, the cover plate 54 is detachably connected to the low temperature liquefied gas container 57, and the low temperature liquefied gas supply port 64 and the vaporized gas exit 65 opened at the container 57 are provided at the same cover plate 54. Therefore, the inner tank 53 containing the tube 1 together with the refrigerant 7 and the outer tank 56 sealing the heat exchanging medium are integrally formed, the apparatus can be formed in very small size as compared with the low temperature liquefied gas container 57, and can accordingly be simply transported. Thus, the apparatus of this embodiment can be readily transported to the field, and the fertilized ova, spermatozoa or the like collected in the field can be immediately preserved in the refrigerant 7, e.g., Freon or the like. Thereafter, the apparatus of freezing fertilized ova, spermatozoa or the like of the invention can be installed in the liquefied nitrogen gas container 57 sold in the market and capable of being obtained readily. Accordingly, the death rate of the fertilized ova, spermatozoa or the like can be remarkably reduced as compared with the conventional example, thereby improving the yield.

The apparatus of this invention is simply fabricated with less number of members as main members of the columns 52, 55 of different diameter and the cover plate 54, and the inner tank 53 may be small enough. Therefore, the motor M of the agitator 59 may be small type and light weight inexpensively.

Still another preferred embodiment of the apparatus for freezing fertilized ova, spermatozoa or the like for performing the method of the present invention will now be described with reference to FIG. 15 in which the structure and operation are simplified for effectively performing the objects of the present invention.

In FIG. 15, the apparatus of this embodiment has a cooling tank 70, an openable cover 71 for the tank 70, refrigerant 7, e.g., methyl alcohol, Freon or the like contained in a predetermined quantity in the cooling tank 70 and to be cooled suitably by cooling means such as a refrigerating machine or the like at an adequate time, and a vapor phase portion 9 formed in the upper portion of the refrigerant 7 in the tank 70.

The apparatus of this embodiment further has a tube erecting trestle 72 dipped in the refrigerant 7 at the bottom 70' of the cooling tank 70, a side frame 74 stood from a base 73 at the trestle 72, and a porous plate 76 perforated with through holes 75, 75' and laterally mounted directly above the base 73 at the base of the side frame 74, and tubes 1, 1, . . . inserted into the holes 75, 75' and erected on the base 73.

The tubes 1, 1, . . . thus erected are dipped at the lower half portions in the refrigerant 7, and extend at the upper half portions from the refrigerant 7 to the vapor phase portion 9.

A heat transfer block 77 formed of heat transfer substance, e.g., copper or the like is engaged and placed on the top ends 1', 1', . . . of the tubes 1, 1, . . . extending to the vapor phase portion 9 in the tank. In the exemplified example in FIG. 15, engaging recesses 78, 78, . . . are perforated on the lower surface of the block 77 to engage the top ends 1', 1', . . . of the tubes 1, 1, . . . and refrigerant storage recess 79 is formed on the top surface of the block 77 to contain refrigerant, e.g., liquefied nitrogen LN, dry ice or the like in the recess 79. Heat transfer block supporting edges 80 are projected from the top of the side frame 74 as shown.

To freeze the articles 3 to be frozen, e.g., fertilized ova, spermatozoa or the like with the apparatus thus constructed according to this invention, the tubes 1, 1, . . . are erected on the trestle 72 as described above, are dipped at the lower half portions in the refrigerant, the heat transfer block 77 is engaged and placed on the top ends 1', 1', . . . extending of the tubes 1, 1, . . . into the vapor phase portion 9 in the tank, the refrigerant 7' is first contained in the refrigerant storage recess 79, thereby cooling the top ends 1', 1', . . . of the tubes 1, 1, . . . through the heat transfer block 77 via the cooling head of the refrigerant 7', and the upper buffer solution segment 2b is frozen. At this time the refrigerant 7 is not yet frozen, and the lower buffer solution segment 2a is not yet frozen.

Then, the refrigerant 7 is cooled by cooling means, e.g., refrigerating machine or the like, thereby lowering the temperature of the lower buffer solution segment 2a to its freezing point. Thus, the crystalline nuclei in the upper buffer solution segment 2b will gradually grow and hence completely freeze the lower buffer solution 2a without overcooling.

As described above, the apparatus of this embodiment thus constructed according to the present invention is constructed in the arrangement that the cooling tank 70 capable of being cooled suitably by desired means at the refrigerant 7 contained therein and a plurality of required tubes I, 1, . . . containing the articles 3 to be frozen, e.g., fertilized ova, spermatozoa or the like in the buffer solution 2 are dipped in the refrigerant 7 and erected therein, the tube erecting trestle 72 extending and supporting the tubes in the vapor phase portion 9 formed in the upper portion of the cooling tank 70 and the heat transfer block 77 engaged and placed on the top ends 1', 1', . . . of the tubes 1, 1, . . . in the upper vapor phase portion 9 of the cooling tank 70 are provided, and the refrigerant storage recess 79 is formed on the block 77. Therefore, the tubes 1, 1, . . . are erected on the trestle 72, the heat transfer block 77 is engaged and placed thereon, the refrigerant 7' is filled in the recess 79, and the refrigerant 7 is then cooled by simple operation, thereby effectively freezing the refrigerant, and the tubes 1, 1, . . . through the heat transfer block 77. In this manner, the freezing of the articles to be frozen, e.g., fertilized ova, spermatozoa or the like can be performed with high reliability without overcooling of the lower buffer solution segment 2a containing the same, with simplified entire construction inexpensively.

What is claimed is:

1. An apparatus for freezing fertilized ova, spermatozoa or the like comprising:

a tube containing a first buffer solution containing articles to be frozen such as fertilized ova, spermatozoa or the like and a second buffer solution containing no articles to be frozen, and a refrigerant for cooling the first and second buffer solution, a low constant temperature tank containing the refrigerant and a cover plate covered thereon, a guide rod vertically mounted on the cover plate of said tank, upper and lower mounting members of synthetic resin mounted on said guide rod, and a slide pin of synthetic resin for holding said tube and elastically urged by a spring downwardly to be elevationally movably mounted at said upper mounting member, thereby elastically holding said tube between said slide pin and said lower mounting member.

2. The apparatus as claimed in claim 1, wherein said upper mounting member is elevationally adjustably formed at said guide rod.

3. The apparatus as claimed in claim 1, wherein said slide pin is formed of a tube inserting port of downward recess formed at the center, and a sensor hole of upward opening at the center communicating with said inserting port.

4. An apparatus for freezing fertilized ova, spermatozoa or the like comprising:

a tube containing a first buffer solution containing articles to be frozen such as fertilized ova, spermatozoa or the like, a second buffer containing no articles to be frozen, and a refrigerant for cooling the first and second buffer solutions, an inner tank containing the refrigerant and a cover attached to the upper edge of said inner tank, an outer tank sealing heat exchanging medium such as helium at the outer peripheral side of said inner tank and integrally formed with said inner tank, a tube erecting base detachably sealed in the refrigerant in said inner tank, predetermined members such as an agitator, a heater and a thermometer sealed in the refrigerant in said inner tank, the cover of the said inner tank being detachably mounted in a low temperature liquefied gas container, and having a low temperature liquefied gas supply port opened within said container and a vaporized gas exit opened thereat.

5. The apparatus as claimed in claim 4, wherein said tube erecting base comprising a horseshoe-shaped tube supporting base and a guide and handle stood from said supporting base with horseshoe-shaped tube holder longitudinally slidably mounted thereat.

6. An apparatus for freezing fertilized ova, spermatozoa or the like comprising:

a plurality of tubes each having a first buffer solution containing no articles to be frozen such as fertilized ova, spermatozoa or the like, a second buffer solution containing articles to be frozen in the lower half portion thereof, and a refrigerant dipping said tubes erected therein for cooling the first and second buffer solutions, a cooling tank suitably capable of being cooled by predetermined means via the refrigerant contained therein at a predetermined time, a tube erecting trestle for supporting said tubes to extend in vapor phase formed in the upper portion of said cooling tank, and a heat transfer block engaged and placed on the upper ends of said tubes in the vapor phase portion of said tank and containing refrigerant storage recess formed thereon for $LN_2$, or dry ice.

7. The apparatus as claimed in claim 6, wherein said heat transfer block comprises a plurality of engaging holes formed on the lower surface thereof for engaging the top ends of said tubes and a refrigerant storage recess formed on the upper surface thereof for containing cooling source.

* * * * *